(12) United States Patent
Mamone et al.

(10) Patent No.: US 9,783,842 B2
(45) Date of Patent: Oct. 10, 2017

(54) STR GENOTYPING BY DIFFERENTIAL HYBRIDIZATION

(71) Applicant: TECAN TRADING AG, Mannedorf (CH)

(72) Inventors: Joseph Mamone, Hillsborough, NJ (US); Marc N. Feiglin, East Brunswick, NJ (US); Howard Gamper, Philadelphia, PA (US)

(73) Assignee: Tecan Trading AG, Mannedorf (CH)

( * ) Notice: Subject to any disclaimer, the term of this patent is extended or adjusted under 35 U.S.C. 154(b) by 340 days.

(21) Appl. No.: 14/372,796

(22) PCT Filed: Jan. 18, 2013

(86) PCT No.: PCT/EP2013/050936
§ 371 (c)(1),
(2) Date: Jul. 17, 2014

(87) PCT Pub. No.: WO2013/107857
PCT Pub. Date: Jul. 25, 2013

(65) Prior Publication Data
US 2015/0010908 A1    Jan. 8, 2015

Related U.S. Application Data

(63) Continuation of application No. 13/352,742, filed on Jan. 18, 2012, now abandoned.

(51) Int. Cl.
*C12Q 1/68* (2006.01)
(52) U.S. Cl.
CPC ......... *C12Q 1/6813* (2013.01); *C12Q 1/6827* (2013.01); *C12Q 2525/151* (2013.01); *C12Q 2525/186* (2013.01)

(58) Field of Classification Search
None
See application file for complete search history.

(56) References Cited

U.S. PATENT DOCUMENTS

| 6,395,493 | B1 | 5/2002 | Sosnowski et al. |
| 2006/0257916 | A1* | 11/2006 | Hashmi ................ B82Y 5/00 435/6.12 |
| 2011/0003290 | A1 | 1/2011 | Gale et al. |

FOREIGN PATENT DOCUMENTS

WO    WO 96/36731    11/1996

OTHER PUBLICATIONS

Dsouza et al. Chemical Reviews 2011; 111: 7941-7980.*

* cited by examiner

*Primary Examiner* — Angela M Bertagna
(74) *Attorney, Agent, or Firm* — Notaro, Michalos & Zaccaria P.C.

(57) ABSTRACT

In a method of deducing the number of repeat units in a selected short tandem repeat (STR) in a genomic sample, at least a single stranded target DNA generated from a genomic sample comprising a selected STR, an STR probe (P1,P1'), a reference probe (P2), and two blockers (B1,B2) are provided, and at least three differential hybridization experiments are carried out, based on which the number of STR probe oligonucleotides (P1,P1') bound per target DNA strand in each differential hybridization experiment is determined. The method further comprises the step of comparing these numbers of STR probe oligonucleotides (P1,P1') bound per target DNA strand in the differential hybridization experiments for deducing the number of repeat units in the selected STR on the single stranded target DNA strand. Also disclosed are kits for carrying out STR genotyping by differential hybridization.

14 Claims, 4 Drawing Sheets

Figure 12A:
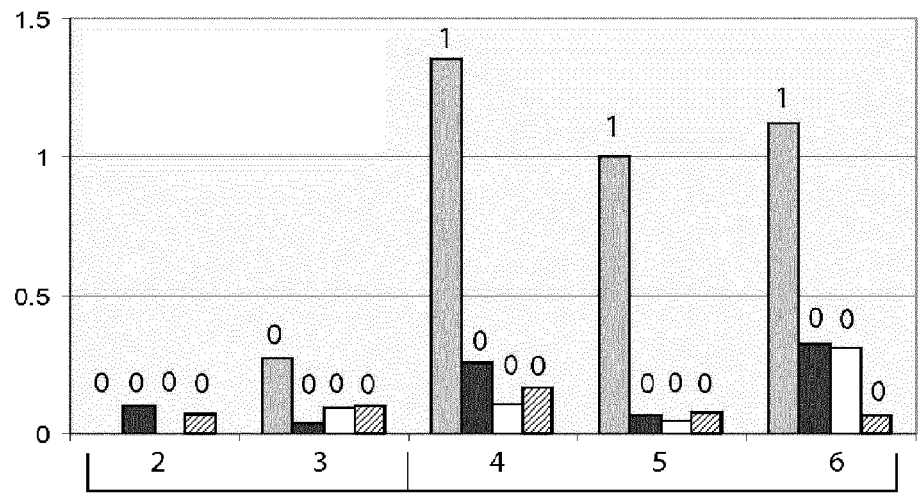

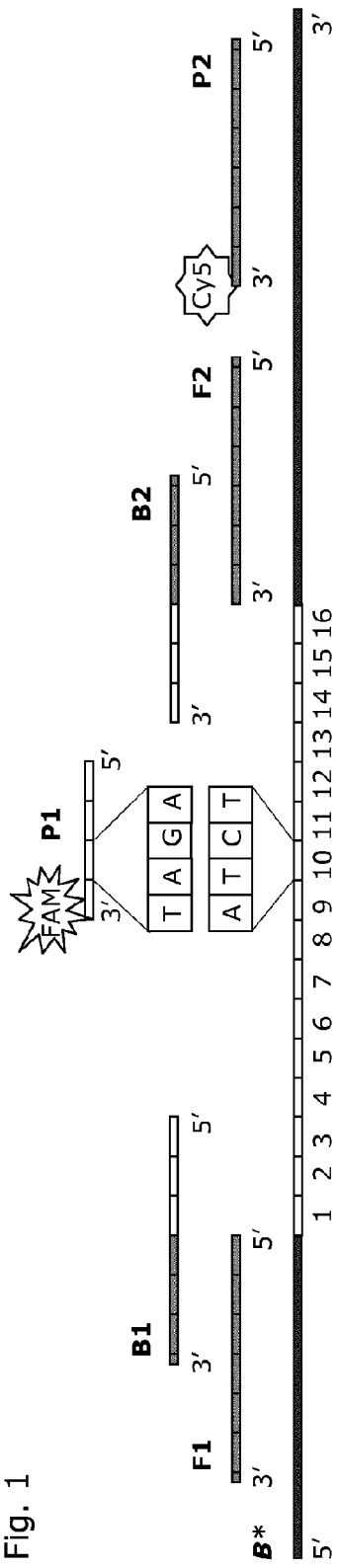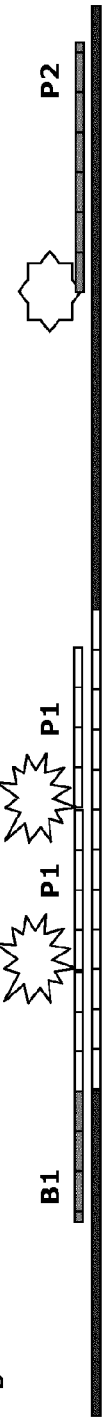
Fig. 1
Fig. 2
Fig. 3
Fig. 4
Fig. 5

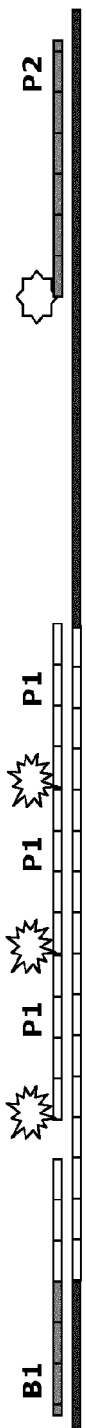
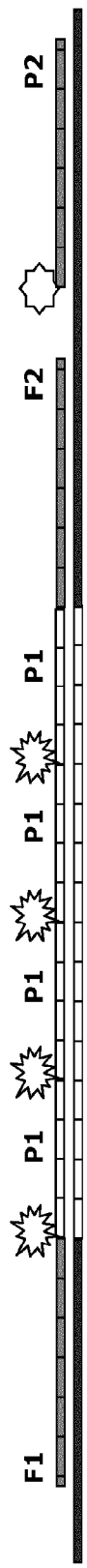
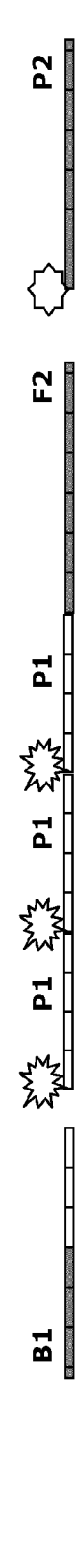
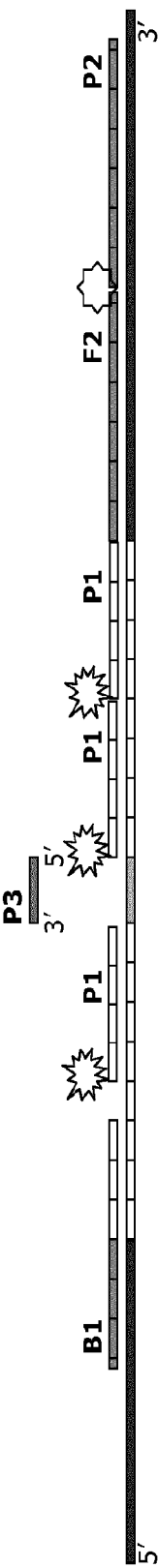
Fig. 6
Fig. 7
Fig. 8
Fig. 9
Fig. 10
Fig. 11

Fig. 13

STR GENOTYPING BY DIFFERENTIAL HYBRIDIZATION

CROSS-REFERENCE TO RELATED APPLICATIONS

This international patent application claims priority of the U.S. patent application Ser. No. 13/352,742, filed on Jan. 18, 2012, which is incorporated herein by reference in its entirety and for all purposes.

FIELD OF TECHNOLOGY

The present invention relates to a method of analyzing short tandem repeats according to the preamble of the independent claim 1. A brief overview over the actual field of technology, commercial kits, DNA separations, recovery of information from degraded DNA, and perspectives of the future dealing with short tandem repeats (STRs) that are sometimes also referred to as micro-satellites or simple sequence repeats (SSRs) is given by John M. Butler in the Mini-Review "Short tandem repeat typing technologies used in human identity testing" (*BioTechniques* 2007, Suppl. to Vol. 43, No. 4).

RELATED PRIOR ART

The analysis of short tandem repeats (STRs) of individual human genomes is routinely used, e.g. in human identity testing, and in testing of other organisms like plants and cells. Such short tandem repeats are simple sequence motifs of a few up to several dozen repeat units. The human genome comprises thousands of such STRs, which are typically located in non-coding regions. As STRs are polymorph with respect to their number of repeat units, human individuals may be distinguished from each other by the unique number of repeat units per allele and per STR locus. Therefore, the analysis of STRs has turned out to be particularly useful in the identification of human individuals, e.g. in forensic medicine or parentage testing.

Typically, the analysis of STRs involves as a first step the isolation of genomic DNA of human individuals, followed by a Polymerase Chain Reaction (PCR) amplification step. Here, specific, selected STR loci are amplified, and multiplexing (the amplification of multiple STR loci simultaneously) has become routine in biological laboratories. This allows that in a single test a high discrimination rate may be achieved due to the assessment of several STRs in parallel, while only minor amounts of DNA have to be employed. This in turn is of particular relevance in forensic medicine, where often only minor amounts of DNA are available (a large portion of DNA may be degraded).

Depending on the aim of the analysis (e.g. human identification, parentage testing, population analysis), different STRs may be used. In particular when DNA profiles should be compared among different laboratories, standardization of STR analysis is an important aspect. For example, there are at least seven well established Interpol STR loci that are used for STR analysis in European forensic laboratories (see Gill et al., "The evolution of DNA databases—Recommendations for new European STR loci", Forensic Science International, 156 (2006), 242-244). This standardization of analyzed STR loci allows a direct comparison of DNA profiles throughout the different laboratories involved.

After the amplification step of selected genomic fragments, the length of each amplified STR is determined. Fragment length determination is widely done using e.g. capillary electrophoresis. Here, the amplified DNA products are separated by electrophoresis and detected by comparison to a standardized allelic ladder. Advantages of DNA length determination using capillary electrophoresis include highly precise sizing (e.g. to less than 1 nucleotide), multiplexing by size by making some amplicons bigger than others but labeling all amplicons with the same fluorescent label (increases throughput). Utilizing capillary electrophoresis provides the advantage that mixtures are much more easily interpreted since intensity and size data are both available to the analyst. However, capillary electrophoresis requires the use of large instruments (e.g. the ABI 3730 Genetic Analyzer, Applied Biosystems). This increases the incurring costs and the complexity of the application. Additionally, the relatively long sample run times reduce the sample throughput and thus can result in backlogs in the respective laboratory. Further advantages of capillary electrophoresis comprise that commonly used instruments with significant installed base in genomic laboratories can be utilized and STR analysis is more easily automatable than prior generation of slab gel electrophoresis. Since capillary electrophoresis does not directly interrogate nucleotide sequences, micro-heterogeneity of the STR due to sequence substitutions are not detected if the STR is of the same length; thus, important information can be lost. Moreover capillary electrophoresis instrumentation is delicate, expensive, and sensitive to dust and movement. The detection window (signal between noise at the low end and maxed out at the high end) is relatively narrow, necessitating expensive, time consuming, and cumbersome quantitative PCR quantification of DNA and normalization to get into the "sweet spot".

Other approaches include the use of hybridization techniques for STR fragment length determination. For example, in the document WO 96/36731, the number of repeats is determined by hybridizing a target DNA with a unique set of complementary probes containing tandem repeats of known length. If a probe containing more repeats than the target DNA hybridizes, a loop structure is formed, while hybridization of a probe with the identical number of repeats, no loop structure is formed. The length is then identified using the different fluorescent labels of the various probes without using electrophoretic separation. This is a multistep process involving digestion with a nuclease specific to S—S bonds and labeling with a DNA polymerase. This method requires synthesis of a solid supported oligonucleotide array, and therefore cannot be done in solution.

In the document U.S. Pat. No. 6,395,493 B1 a method for determination of length polymorphism in DNA is disclosed, which also involves a hybridization reaction. This document describes an assay that involves the use of a silicon microchip composed of an arrayed set of electrodes that each contain a unique "capture probe" for each possible allele of each possible STR loci of interest. For example, in order to determine which of the possible eight alleles at the TPDX locus (e.g., 6-13 repeats) are present; eight different probe sites are required. The DNA sample of interest is amplified and then washed over the chip. It will hybridize to the electrodes with complementary capture probes. The "capture probe" captures the PCR-amplified STR allele by binding to the repeat region and 30-40 bases of the flanking region. After hybridization, an "electronic stringency" is then applied to each probe site by simply adjusting the electric field strength. Samples that are not a perfect match for the probe will be denatured and driven away from the probe.

After removing unbound and denatured DNA, a mixture of "reporter probes" is washed over the chips. The "reporter probe" contains 1-3 repeat units, some flanking sequence and a fluorescent dye. This probe will hybridize to the STR allele of DNA captured on the chip and generates a fluorescence signal at the probe site that can be interpreted to yield the sample's genotype. The read-out provides a genotype that corresponds to the number of repeats present in the sample even though no size-based separation has been performed.

In the method described in the document U.S. Pat. No. 6,395,493 B1, an array of capture probes must be "printed" (i.e. immobilized) on the surface of the reaction vessel and the DNA is subsequently washed over this array. As this method requires pre-printing or purchase of a special pre-printed array, the intensity of the read-out signal is limited by the number of capture oligonucleotides printed on each electrode. Further amplification of the DNA sample cannot increase signal beyond the number of capture electrodes. Furthermore, the method described requires special instrumentation to denature mismatched hybrids prior to washing. The method according to the present invention however requires no such special instrumentation (see below the advantages of the present invention).

From the document US 2011/0003290 A1, a method for detecting the number of tandem repeats, e.g. in an STR locus in a target polynucleotide is known which uses a melting temperature analysis. In this method, a fluorescently labeled probe oligonucleotide is used which comprises a sequence of at least 5 nucleotides complementary to at least one of the tandem repeats. The length of the probe oligonucleotide is chosen so that the melting temperature differs in hybrids generated by the probe oligonucleotide when different numbers of tandem repeats are present in a selected STR locus. The number of tandem repeats may then be determined by a melting curve analysis, in which the melting temperature is determined by a kinetic measurement the fluorescence upon controlled temperature changes.

Objects and Summary of the Present Invention

It is an object of the present invention to suggest a method of deducing the number of tandem repeats in a nucleic acid sample.

According to a first aspect, this object is achieved by a method of deducing the number of repeat units in a selected short tandem repeat (STR) in a genomic sample according to the present invention. The method as herein disclosed comprises the steps of:
a) providing at least:
  a1) a single stranded target DNA generated from a genomic sample comprising a selected STR;
  a2) an STR probe (P1,P1') with a first fluorescent label, the at least one STR probe (P1,P1') being an oligonucleotide which comprises a sequence complementary to a defined number of repeat units of the selected STR on the single stranded target DNA;
  a3) a reference probe (P2) with a second fluorescent label, which is different from the first fluorescent label, the reference probe (P2) being an oligonucleotide which comprises a sequence complementary to a 5'- or a 3'-flanking sequence of the selected STR on the single stranded target DNA;
  a4) two blockers (B1,B2) which are oligonucleotides, wherein a first blocker (B1) comprises a sequence complementary to a sequence of the 5' flanking region of the STR and to at least one of the STR repeat units adjacent to that 5' flanking region, and wherein a second blocker (B2) comprises a sequence complementary to a sequence of the 3' flanking region of the STR and to at least one of the STR repeat units adjacent to that 3' flanking region;
b) carrying out at least the following three differential hybridization experiments by mixing in each experiment an amount of the single stranded target DNA with:
  b1) the at least one STR probe (P1,P1') and the reference probe (P2), and allowing hybridization to the single stranded target DNA in a first differential hybridization experiment;
  b2) the at least one STR probe (P1,P1'), the reference probe (P2) and one of the at least two blockers (B1,B2), and allowing hybridization to the single stranded target DNA in a second differential hybridization experiment; and
  b3) the at least one STR probe (P1,P1'), the reference probe (P2) and the two blockers (B1,B2), and allowing hybridization to the single stranded target DNA in a third differential hybridization experiment;
c) measuring for each differential hybridization experiment the intensity of the fluorescence provided by the at least one STR probe (P1,P1') bound to the repeat units of the selected STR;
d) measuring for each differential hybridization experiment the intensity of the fluorescence provided by the reference probe (P2) bound to one of the flanking sequence of the single stranded target DNA;
e) correlating for each differential hybridization experiment the fluorescence intensity of the at least one STR probe (P1,P1') measured in step c) to the fluorescence intensity of the reference probe (P2) measured in step d), thereby determining for each differential hybridization experiment the number of STR probe oligonucleotides (P1,P1') bound per target DNA strand, and
f) comparing the number of STR probe oligonucleotides (P1,P1') bound per target DNA strand determined for the differential hybridization experiments for deducing the number of repeat units in the selected STR on the single stranded target DNA strand.

According to a second aspect, this object is achieved by proposing kits for carrying out STR genotyping by differential hybridization as herein disclosed.

Additional features of the present invention and preferred embodiments are herein disclosed as well.

Advantages of the Method According to the Present Invention Comprise:

The assessment of the number of repeats may be done using standard microplate fluorescence readers instead of large capillary electrophoresis devices. Such fluorescence readers are often already available in typical forensic, medical or diagnostic laboratories, and of even more importance: such a standard microplate fluorescence reader costs about 10% of a capillary electrophoresis device (the latter being about US $ 200,000).

The analysis time can be reduced, as first results may be obtained faster than in capillary electrophoresis.

The method of the current invention is simpler than conventional analysis methods, as the method is not enzymatic.

This method is sequence specific (versus sizing), so microvariants can be detected by inclusion of additional probes.

The present method is less sensitive to input DNA since a simple fluorescence measurement e.g. in a standard microplate fluorescence reader has a broader signal dynamic range than the detectors and data analysis algorithms used e.g in capillary electrophoresis devices. An additional step of quantifying the DNA prior to capillary electrophoresis analysis is required to ensure the signal peaks are strong enough to be above the background noise and not so strong to exceed the linear detection range; this "signal window" typically is significantly wider with direct fluorescence reading when applying the method of the current invention.

The presented method is faster (not including the time required for sample preparation, e.g. purification and amplification), as it is based on a direct fluorescence measurement in the reaction vessels which may be analyzed instantaneously, without involving a lengthy kinetic measurement or capillary electrophoresis. Thus, a user can analyze e.g. the 13 CODIS loci on 7 different samples on a single 384 well microplate or 29 samples on a 1536 well plate. Such plates can be measured on a typical microplate reader in less than a minute or two. High throughput capillary electrophoresis devices can process up to 16 samples per run with each run taking 1-2 hours.

In contrast to known multistep methods involving digestion with a nuclease that is specific to S—S bonds and labeling with a DNA polymerase, the method of the current invention is much simpler requiring only a few parallel hybridization experiments.

Known multistep methods may require synthesis of a solid supported oligonucleotide array or "printing" such a capture probe array on the surface of the reaction vessel, the DNA then is subsequently washed over this array. In contrast, the present invention binds the DNA to any surface and then washes the probes over the DNA; the hybridization is done in solution and pre-printing or purchasing of a special pre-printed array is not necessary.

Known multistep methods require special instrumentation with precise temperature control to denature mismatched hybrids prior to washing. The inventive method does not require such special instrumentation. In fact, the presented method could be designed as a homogenous assay using quenching probe chemistries such as available from Molecular Beacons or Foerster Resonance Energy Transfer (FRET).

BRIEF INTRODUCTION OF THE DRAWINGS

Figure 12B:
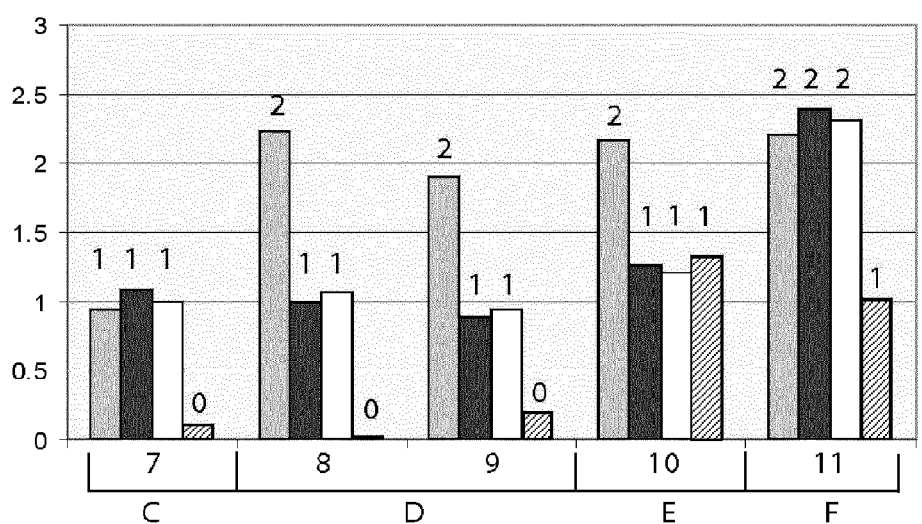

With the help of the drawings, the preferred embodiments of the method and kits of the present invention are illustrated without narrowing the scope of the present invention. It is shown in:

FIG. 1 a schematic overview over a typical kit comprising various oligonucleotides for carrying out the method of genotyping the human CSF1PO STR by differential hybridization;

FIGS. 2-11 a schematic illustration of some possible hybridization results that are theoretically achievable by the method and kits of the present invention, wherein it is shown in:

FIG. 2 a group A CSF1PO target DNA with 2 tetranucleotide repeats without blocking oligonucleotides (blocking oligos) and flanking oligonucleotides (flanking oligos), and with no hybridization of an STR probe;

FIG. 3 a group B CSF1PO target DNA with 4 tetranucleotide repeats with one blocking oligo, and with no hybridization of an STR probe;

FIG. 4 a group C CSF1PO target DNA with 7 tetranucleotide repeats with one blocking oligo, and with hybridization of one STR probe;

FIG. 5 a group G CSF1PO target DNA with 12 tetranucleotide repeats with one blocking oligo, and with hybridization of two STR probes;

FIG. 6 a group J CSF1PO target DNA with 16 tetranucleotide repeats with one blocking oligo, and with hybridization of three STR probes;

FIG. 7 a group J CSF1PO target DNA with 16 tetranucleotide repeats with two flanking oligos, and with hybridization of four STR probes;

FIG. 8 a group J CSF1PO target DNA with 16 tetranucleotide repeats with two blocking oligos, and with hybridization of two STR probes;

FIG. 9 a group J CSF1PO target DNA with 16 tetranucleotide repeats with one flanking oligo and one blocking oligo, and with hybridization of three STR probes; and in FIG. 10 a group J CSF1PO target DNA with 16 tetranucleotide repeats with one blocking oligo and one flanking oligo, and with hybridization of three STR probes;

FIG. 11 a target DNA with a non STR island sequence located in the STR fragment of a group J CSF1PO target DNA with 16 tetranucleotide repeats; with one blocking oligo and one flanking oligo, with hybridization of three STR probes, and with projected hybridization of an insert probe with a nucleotide sequence complimentary to the island sequence;

FIG. 12 diagram showing a combination of theoretical expectations and achieved results of experiments as carried out with FAM-labeled 16-mer probes $(5'-AGAT)_4$ hybridized to a series of chemically synthesized single-stranded DNAs which contained 2-16 ATCT repeats, wherein it is shown in:

FIG. 12A the groups A and B of target DNA;

FIG. 12B the groups C, D, E, and F of target DNA; and in

Figure 12C:
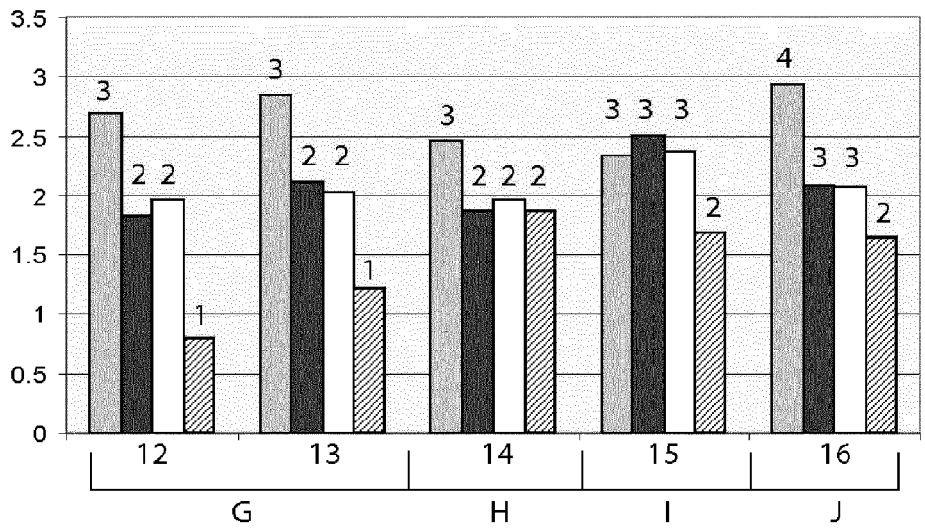

FIG. 12C the groups G, H, 1 and 3 of target DNA;

Figure 13:
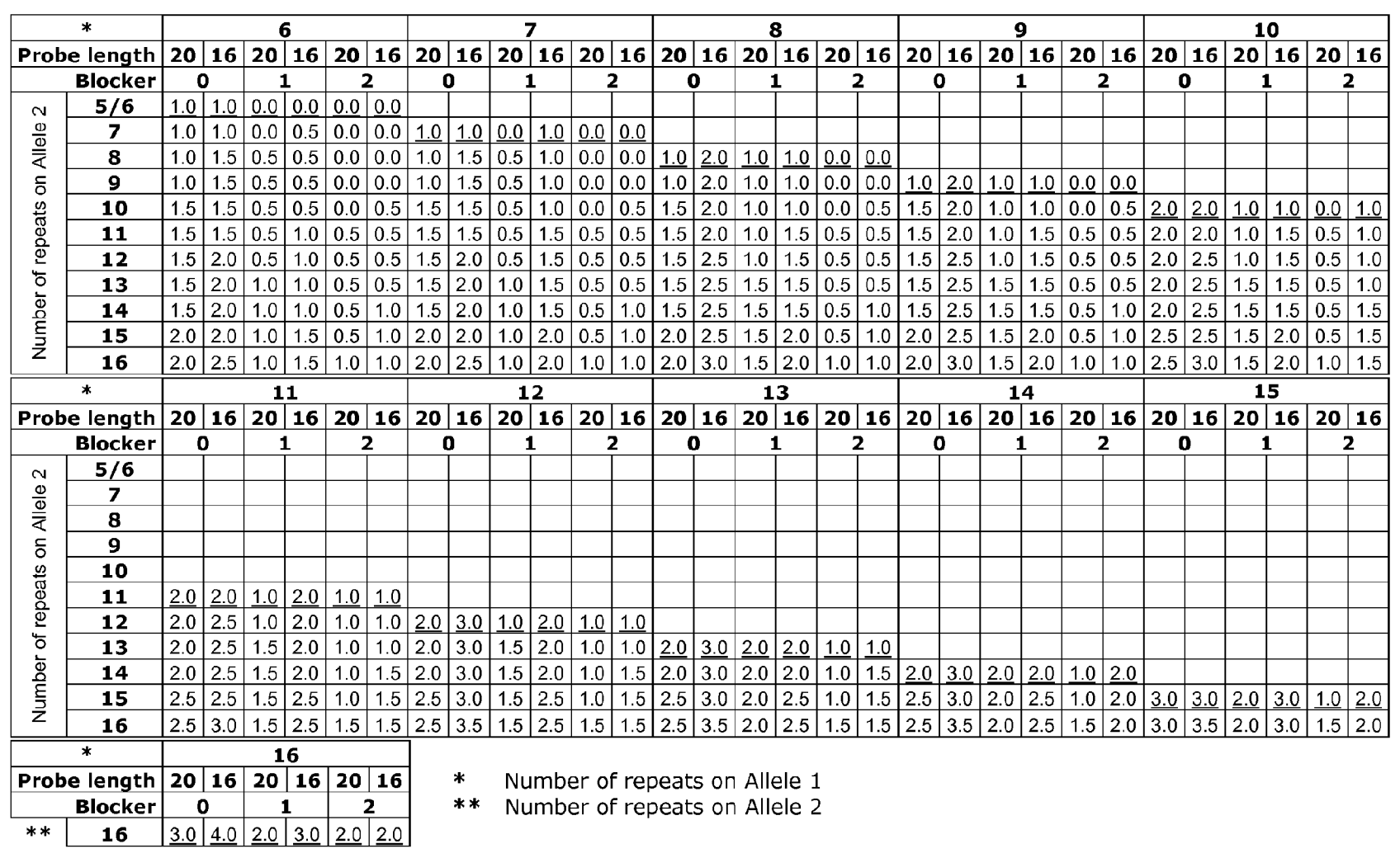

FIG. 13 a table diagram displaying the results obtained from allele pairs in STR assays.

DETAILED DESCRIPTION OF THE PRESENT INVENTION

The present invention relates to the detection of the number of repeats in selected STR loci. According to the present invention, the number of repeat units is correlated to the signal intensity of parallel hybridization experiments. For this, the number of labeled, repeat-specific probes that bind to a repeat is correlated positively to the number of repeats present. Comparison of bound repeat probe signal to signal from a stoichiometrically binding reference probe outside the repeat region allows determination of the number of repeat probes bound per molecule and reduces the sensitivity of the method to the amount of DNA used. By making hybridization measurements in several parallel experiments, whereby a known number of the available repeats are blocked from hybridization in parallel experiments, it is possible to deduce the number of repeats present. Optionally, the signal response of the several experiments can be compared to results obtained empirically in model systems of known repeat numbers to achieve high confidence results.

Selection of STR Loci:

The method according to the present invention is particularly useful for identifying human individuals. However, the analysis of STRs is not restricted to human genomic DNA, but may be used e.g. in the analysis of animals, plants, or microorganisms. Exemplarily, the analysis of STRs for food authentication or in the quality control of mammalian and eukaryotic cell lines shall be mentioned here.

For human identification it is proposed to use the STR loci that are generally accepted by the respective law enforcement agency. The two major sets are the 13 FBI (US Federal Bureau of Investigation) CODIS Loci and the 10 FSS (United Kingdom Forensic Science Service) SGM and SGM plus loci. Non-human DNA testing and microbial forensics is described by John M. Butler in "Forensic DNA Typing, Biology, Technology, and Genetics of STR Markers" (Elsevier Academic Press, Second Edition 2005; see chapter 11, pages 299-330). There, cat and dog STRs are described (and the sources referenced) as well as plant STRs (e.g. *Cannabis sativa*) and it is pointed out that "as with human STRs, marijuana STR markers are highly polymorphic, specific to unique sites in the genome, and capable of deciphering mixtures. A heaxanucleotide repeat marker showed repeat units ranging from 3-40 in 108 tested marijuana samples, and primers amplifying this locus produced no cross-reactive amplicons from other 20 species of plants tested (Hsieh et al 2003)". From microbial forensics, first steps are reported in connection with bioterrorism, including genome sequencing of *Bacillus anthracis* (anthrax) and phylogenetic analyses of viral strains of HIV.

Among the various types of STR systems, tetranucleotide repeats (4 repeat units in the core repeat) have become more popular for genotyping than di- or trinucleotides (2 or 3 repeat units). Penta- and hexanucleotides (5 or 6 repeat units) repeats are less common in the human genome but are being examined by some laboratories (see Butler 2005, page 89, 3$^{rd}$ paragraph). The method according to the present invention is not restricted to a particular number of nucleotides in a repeat unit.

PCR:

A PCR amplification step is necessary when working with STR systems because genomic DNA would be too complex for hybridization assays. Multiplex PCR, where a defined number or a combination of STR loci is treated simultaneously is possible. There actually is no maximum or minimum number of STRs; everything that is empirically possible is preferred. A large number of STR markers have been characterized by academic and commercial laboratories for use in disease and gene location studies. For example, the Marshfield Medical Research Foundation in Marshfield, Wis. (marshfieldclinic.org) has gathered genotype data ob over 8000 STRs that are scattered across the 23 pairs of human chromosomes (see Butler 2005, page 86). There exist many commercial kits, e.g. from Applied Biosystems, Promega, and Qiagen, to accomplish the appropriate multiplex. However, other methods suitable for the amplification of specific sequences of a genomic DNA sample, such as strand displacement amplification methods may be used for amplifying one or more selected STR loci from the genomic sample.

Used Oligonucleotides:

The analysis of one or more selected STRs in a genomic sample according to the present invention is carried out using a combination of distinct oligonucleotides, which are specifically designed for each single STR locus and which are used in at least three different hybridization experiments. Such oligonucleotides according to the present invention are:

one or more STR probes P1, P1' specific to the sequence of the STR repeat, a reference probe P2 for normalization, two or more blockers B1, B2 and, two or more flankers F1, F2.

In each hybridization experiment, at least one STR probe P1,P1' is used with the reference probe P2 for normalization, that is for determining the number of STR probe oligonucleotides P1,P1' bound per target molecule. Additionally, the STR and reference probes may be combined in separate hybridization experiments e.g. with one or more of the blockers B1,B2 and/or one or more of the flankers F1,F2. When different oligonucleotides are used as a mixture in one hybridization experiment according to the present invention, the preferred oligonucleotides are chosen with respect to their melting temperature ($T_m$) that binding of all oligonucleotides used is possible at the hybridization temperature (at the temperature a hybridization experiment is carried out). Accordingly, the hybridization temperature of the experiment should be lower than the $T_m$ of the oligonucleotides used (detailed description see below).

Strategy of genotyping of the human CSF1PO STR by differential hybridization: CSF1PO is a short tandem repeat (STR) known to be composed of 5-16 consecutive repeats of the 5'-ATCT-3'-tetramer located at a unique position in human chromosome 5. To differentiate between the repeat numbers, to deduce or even to determine the number of repeat units, a novel hybridization approach according to the present invention was applied. In this approach, for demonstrational purposes a FAM-labeled 16-mer probe (5'-AGAT-3')$_4$ was hybridized to a series of chemically synthesized single-stranded DNAs which contained 2-16 5'-ATCT-3' repeats. Each of these 5'-ATCT-3' repeats was embedded in the middle of a longer unrelated sequence which was biotinylated at the 5'-end (see FIG. 1). In FIG. 1 for illustration purposes, tetranucleotide repeats of the STRs in the single-stranded target DNA are indicated in each case as one box and sixteen such tetranucleotide 5'-ATCT-3' repeats in the single-stranded target DNA are indicated by the boxes numbered 1-16. The site at the 5'-end of the single-stranded target DNA is marked with B* that stands for biotinylated. As well know in the art of nucleic acid manipulation in biochemistry, such biotinylation enables binding of target DNA molecules to streptavidin-coated magnetic beads. The DNA fragment from the 5'-end to the beginning of the STRs is called 5'-flanking region and the DNA fragment from the 3'-end of the STRs to the 3'-end of the DNA is called 3'-flanking region.

In FIG. 1 it is schematically shown an overview over a kit comprising various oligonucleotides for carrying out the method of genotyping of the human CSF1PO STR by differential hybridization. Such a kit at least comprises an STR probe P1 for hybridizing with a target STR and a reference probe P2 for identification of the relevant single-stranded target DNAs and for normalization of the STR probe signal. In this approach, it is preferred that the STR probe P1 contains four repeats of the four nucleotides 5'-AGAT-3' and is labeled with a first fluorescent label at the 3'-end, which is FAM in this case. FAM (Applied Biosystems Inc.) is a fluorescein derivative and a member of the xanthene fluorescent dyes. Preferably, the reference probe P2 is configured as a 25-mer which is complementary to the region of the target DNA indicated in FIG. 1, e.g. the 3'-flanking region. Alternatively, the reference probe P2 might be configured to be complementary to the 5' flanking region of the selected STR. It is further preferred that the reference probe P2 is labeled with a second fluorescent label. This second fluorescent label is different from the first fluorescent label of the STR probe and is in this case a cyanine dye, e.g. Cy5.

In general, any discernible labeling that allows discrimination of the two probes can be applied to the STR probe P1 and to the reference probe P2. These can be fluorescent dyes as already indicated; however, also donor-acceptor fluorescent pairs e.g. FAM-3-TAM, or FAM-3-ROX, or FAM-4-ROX as disclosed in U.S. Pat. No. 5,654,419 can be used (the rhodamine derivatives TAM and ROX are dyes of Applied Biosystems Inc.). Even if some alternatives to fluorescence labeling may exist, fluorescence is preferred because of its ability of providing multiple colors, being fast, and being sensitive. However, any sort of measureable label that can be attached to oligonucleotides, e.g. to primers and that can be multiplexed could be used, i.e. radioactive, luminescent, chromogenic, tagged beads, etc.

Preferably, the kit also comprises at least two blockers (blocking oligonucleotide) B1,B2 for hybridizing with a fragment of a target STR and with a fragment of the relevant single-stranded target DNA. Preferably and as depicted in FIG. 1, the blocker (blocking oligonucleotide) B1 bridges the 5'-end of the STRs with the 5' flanking region of the DNA and the blocker (blocking oligonucleotide) B2 bridges the 3'-end of the STRs with the 3'-flanking region of the DNA. Of special preference for this approach are blocking oligonucleotides B1,B2 that are 25-mers which are complementary to the regions of the target DNA indicated in FIG. 1.

Preferably, the kit also comprises at least one flanker (flanking oligonucleotide) F1,F2 for hybridizing with a fragment of the relevant single-stranded target DNA adjacent to the target STRs. Preferably and as depicted in FIG. 1, the flanker (flanking oligonucleotide) F1 hybridizes to the 5'-flanking region from the 5'-end of the STRs in direction to the 5'-end of the single-stranded target DNA and the flanker (flanking oligonucleotide) F2 hybridizes to the 3'-flanking region from the 3'-end of the STRs in direction to the 3'-end of the single-stranded target DNA. Of special preference for this approach are flanking oligonucleotides F1,F2 that are 25-mers which are complementary to the regions of the target DNA indicated in FIG. 1.

Importantly, the flankers F1,F2 hybridize immediately adjacent to the CSF1PO repeat while each of the blocking oligonucleotides B1,B2 hybridizes to 12 nucleotides (3 repeats) of the CSF1PO sequence and to 13 nucleotides of the 5'- or 3'-flanking target sequences. It is also important to note that on the same 5'- or 3'-flanking region of the target DNA, only a blocking oligonucleotide B1,B2 or a flanking oligonucleotide F1,F2 can hybridize; thus, either two blocking oligonucleotides, i.e. B1 & B2, two flanking oligonucleotides, i.e. F1 & F2, or one blocking oligonucleotide plus one flanking oligonucleotide, i.e. B1+F2 or F1+B2 are to be used in a given (parallel) experiment.

The following kits, comprising in each case a distinct set of oligonucleotides for hybridization experiments, are preferred:

a) STR probe P1 and reference probe P2 (also referenced as "XX");
b1) STR probe P1, reference probe P2, with blocker B1 (also referenced as "BX");
b2) STR probe P1, reference probe P2, with blocker B2 (also referenced as "XB");
b3) STR probe P1, reference probe P2, with blockers B1 & B2 (also referenced as "BB");
c1) STR probe P1, reference probe P2, with flanker F1 (also referenced as "FX");
c2) STR probe P1, reference probe P2, with flanker F2 (also referenced as "XF");
c3) STR probe P1, reference probe P2, with flankers F1 & F2 (also referenced as "FF");
d) STR probe P1, reference probe P2, with blocker B1, and flanker F2 (also referenced as "BF");
e) STR probe P1, reference probe P2, with blocker B2, and flanker F1 (also referenced as "FB").

Depending on the actual number of tetranucleotide repeats present in the target DNA, the extent of hybridization of this 16-mer CSF1PO specific STR probe P1 in the presence of the various combinations of these blocking oligonucleotides B1,B2 and flanking oligonucleotides F1,F2, the target DNAs theoretically can be divided into 10 distinct groups A-J of expected hybridization patterns for genotyping this STR and its tetranucleotide repeats (see Table 1).

TABLE 1

Identification of CSF1PO repeat number with a 16-mer probe

| CSF1PO Target | Repeat Number | No Blocker Bases | No Blocker Hybrids | One Blocker Bases | One Blocker Hybrids | Two Blockers Bases | Two Blockers Hybrids | Group |
|---|---|---|---|---|---|---|---|---|
| 12 | 2  | 8  | 0 | 0  | 0 | 0  | 0 | A |
| 13 | 3  | 12 | 0 | 0  | 0 | 0  | 0 |   |
| 14 | 4  | 16 | 1 | 4  | 0 | 0  | 0 | B |
| 1  | 5  | 20 | 1 | 8  | 0 | 0  | 0 |   |
| 15 | 6  | 24 | 1 | 12 | 0 | 0  | 0 |   |
| 16 | 7  | 28 | 1 | 16 | 1 | 4  | 0 | C |
| 2  | 8  | 32 | 2 | 20 | 1 | 8  | 0 | D |
| 17 | 9  | 36 | 2 | 24 | 1 | 12 | 0 |   |
| 18 | 10 | 40 | 2 | 28 | 1 | 16 | 1 | E |
| 19 | 11 | 44 | 2 | 32 | 2 | 20 | 1 | F |
| 3  | 12 | 48 | 3 | 36 | 2 | 24 | 1 | G |
| 20 | 13 | 52 | 3 | 40 | 2 | 28 | 1 |   |
| 21 | 14 | 56 | 3 | 44 | 2 | 32 | 2 | H |
| 22 | 15 | 60 | 3 | 48 | 3 | 36 | 2 | I |
| 4  | 16 | 64 | 4 | 52 | 3 | 40 | 2 | J |

In Table 1, one repeat corresponds to four base pairs (bp); a 16-mer STR probe P1 hybridizes to 4 repeats; each blocking oligonucleotide B1,B2 hybridizes to 3 repeats and interferes with the binding of the STR probe P1 (see also FIG. 1). In the context of this Table 1, the column "Hybrids" indicates the number of STR probes P1 which may bind to the target STR sequence in the given condition.

The FIGS. 2 to 10 schematically illustrate some possible hybridization results that are theoretically achievable by the method and kits of the present invention and that are listed in Table 1.

According to FIG. 2, a group A CSF1PO target DNA with 2 tetranucleotide repeats incubated with kit a) (only containing STR probe P1 and reference probe P2) is expected to show no hybridization of an STR probe P1, because there are not enough nucleotides in the selected STR of the target DNA for achieving stable and substantial hybridization of this STR probe P1 oligonucleotide. The use of additional blockers and/or flankers in parallel experiments would NOT change the result (see below).

According to FIG. 3, a group B CSF1PO target DNA with 4 tetranucleotide repeats incubated with kit b1) (containing STR probe P1, reference probe P2, with one blocker B1) is expected to show no hybridization of an STR probe P1, because there are not enough nucleotides in the selected STR of the target DNA for achieving stable and substantial hybridization of this STR probe P1 oligonucleotide. The additional use of the other blocker B2 (i.e. using kit b3) or the additional use of the flanker F2 (i.e. using kit d) in separate experiments would not change the result.

According to FIG. 4, a group C CSF1PO target DNA with 7 tetranucleotide repeats incubated with kit b2) (containing STR probe P1, reference probe P2, with one blocker B2) is expected to show a single STR probe P1 oligonucleotide hybridizing per target DNA strand, because there are just enough nucleotides in the selected STR present for achieving stable and substantial hybridization of one STR probe P1. The additional use of the flanker F1 in a separate experiment (i.e. using kit e) would not change the result. In contrast, the additional use of the other blocker B1 in a separate experiment (i.e. using kit b3) would considerably change the result, because then there would not be enough nucleotides in the selected STR present in this case for achieving stable and substantial hybridization of an STR probes P1.

According to FIG. 5, a group G CSF1PO target DNA with 12 tetranucleotide repeats incubated with kit b1) (containing STR probe P1, reference probe P2, with one blocker B1) is expected to show two STR probe P1 oligonucleotides hybridizing per target DNA strand, because there are enough nucleotides in the selected STR present for achieving stable hybridization of two STR probe P1 oligonucleotides. The additional use of the flanker F2 in a separate experiment (i.e. using kit d) would not change the number of STR probe P1 oligonucleotides binding to the target DNA strand, but might improve the accessibility of the STR sequence for binding. In contrast, the use of both blockers B1 and B2 (i.e. using kit b3) in a separate experiment would considerably change the result, because then there would be only enough nucleotides in the selected STR present for allowing one STR probe P1 oligonucleotide to stably and substantially hybridize per target DNA strand.

In the FIGS. 6-10, the use of different kits on a CSF1PO target DNA with 16 tetranucleotide repeats in separate experiments and the respective expected results are discussed:

According to FIG. 6, a group J CSF1PO target DNA with 16 tetranucleotide repeats incubated with kit b1) (containing STR probe P1, reference probe P2, with one blocker B1) is expected to show three STR probe P1 oligonucleotides hybridizing per target DNA strand, because there are enough nucleotides in the selected STR present for achieving stable and substantial hybridization of three STR probe P1 oligonucleotides. The additional use of the flanker F2 in a separate experiment (i.e. using kit d) would not change the number of STR probe P1 oligonucleotides binding to the target DNA strand, but might improve the accessibility of the STR sequence for binding. In contrast, the additional use of the other blocker B2 (i.e. using kit b3 in a separate experiment) would considerably change the result, because then there would be only enough nucleotides in the selected STR present any more for achieving stable and substantial hybridization of two STR probe P1 oligonucleotides.

According to FIG. 7, a group J CSF1PO target DNA with 16 tetranucleotide repeats incubated with kit c3) (containing STR probe P1, reference probe P2, with two flanker F1 and F2) is expected to show four STR probe P1 oligonucleotides hybridizing per target DNA strand, because there are just enough nucleotides in the selected STR present for achieving stable and substantial hybridization of four STR probe P1 oligonucleotides.

According to FIG. 8, a group J CSF1PO target DNA with 16 tetranucleotide repeats incubated with kit b3) (containing STR probe P1, reference probe P2, with two blockers B1 and B2) is expected to show two STR probe P1 oligonucleotides hybridizing per target DNA strand, because there just are enough nucleotides in the selected STR present for achieving stable and substantial hybridization of two STR probe oligonucleotides. In a given experiment using both blocker B1,B2, preferably no flanker F1 and/or F2 are used because of competition with the blocker B1 and/or B2 during the hybridization.

According to FIG. 9, a group J CSF1PO target DNA with 16 tetranucleotide repeats incubated with kit e) (containing STR probe P1, reference probe P2, with one flanker F1 and one blocker B2) is expected to show three STR probe P1 oligonucleotides hybridizing per target DNA strand, because there are just enough nucleotides in the selected STR present for achieving stable and substantial hybridization of three STR probe P1 oligonucleotides. Preferably, in such a given experiment no additional blocker B1 and/or flanker F2 is used because of competition with the flanker F1 and/or with the blocker B2 during the hybridization.

According to FIG. 10, a group CSF1PO target DNA with 16 tetranucleotide repeats incubated with kit d) (containing STR probe P1, reference probe P2, with one blocker B1 and one flanker F2) is expected to show three STR Probe P1 oligonucleotides hybridizing per target DNA strand, because there are just enough nucleotides in the selected STR present for achieving stable and substantial hybridization of three STR probe P1 oligonucleotides. Preferably, in such a given experiment no additional blocker B2 and/or flanker F1 is used because of competition with the flanker F2 and/or with the blocker B1 during the hybridization.

The various situations for the exemplarily chosen CSF1PO STR discussed above shall now be supported by practical experiments. The diagrams of FIG. 12 show a combination of the above exercised theoretical expectations and of the actually achieved results. These results have been achieved from experiments that were carried out with FAM-labeled 16-mer probes $(5'\text{-}AGAT)_4$ hybridized to a series of chemically synthesized single-stranded DNAs which contained 2-16 ATCT repeats. It shall be noted here, that alternatively, and preferably, the single stranded target DNA comprising the selected STR is generated from a genomic sample. Naturally occurring human repeats at this particular locus are, as mentioned above, in the range of 5-16 repeats.

EXPERIMENTS

Initially, a series of single-stranded DNAs which contained 2-16 ATCT repeats was chemically synthesized. Each of these 5'-ATCT-3' repeats was embedded in the middle of a longer unrelated sequence corresponding here to the naturally occurring 5' and 3' flanking sequences. The synthetic target DNA's were biotinylated at the 5'-end (see FIG. 1 with a target DNA having 16 tetramer 5'-ATCT-3'-STRs).

Prior to hybridization, the single-stranded target DNA strands as depicted in FIG. 1 were loaded onto a suspension of washed, streptavidine-coated magnetic beads. The binding reactions utilized 0.5 mg of beads and 80 pMoles of each DNA target. It should be noted that capture efficiency usually is greater than 90%.

In addition to a 16-mer STR probe P1 (as indicated in FIG. 1 as well), each hybridization reaction included a Cy5-labeled reference probe P2 and either two flankers (F1 & F2), two blockers (B1 & B2), or one flanker plus one blocker (F1+B2 or B1+F2). Accordingly, the kits b3), c3), d), or e) as defined above have been utilized for hybridization with the single-stranded target DNAs. It is noted here, that alternatively, the kit b1) could have been utilized instead of kit d) and the kit b2) could be utilized instead of kit e), because the same results would have been expected.

The reference probe P2, flankers F1,F2, and blockers B1,B2 used here were 25-mers complementary to the regions of the target DNA indicated in FIG. 1. The flankers F1,F2 hybridized immediately adjacent to the CSF1PO STR repeat while each of the blockers B1,B2 hybridized to 12 nucleotides (3 repeats) of the CSF1PO sequence and to 13 nucleotides of the adjacent flanking target sequence.

For hybridization, 160 pMoles of the Cy5-labeled reference probe P2 together with 160 pMoles each of the desired combination of blockers B1,B2 and flankers F1,F2 were added to 0.5 mg of streptavidine-coated magnetic beads previously loaded with 80 pMoles of a specific single-stranded target DNA. Hybridization was conducted for 5 min at 65° C. followed by 15 min at 37° C. in 100 µl of Buffer A (10 mM Hepes pH 8.0, 50 mM NaCl, 10 mM $MgCl_2$). Next, 160 pMoles of FAM-labeled STR probe P1 was added to the bead suspension. Hybridization of this STR probe P1 to the target DNA was conducted for 15 min at 47° C. After removal of the hybridization solution, the beads were incubated for 15 min at 47° C. in 100 µl of fresh Buffer A. Finally, bound probes were eluted from the washed beads by incubation for 10 min at 65° C. in Buffer B (10 mM Hepes pH 8.0, 15 mM NaCl). Supernatants containing eluted probes were collected and transferred to a microtiter plate for reading of FAM and Cy5 fluorescence in a TECAN INFINITE® 200 microplate reader (Tecan Austria GmbH, Groedig, Austria).

On the horizontal axis of the diagrams in FIG. 12, the number of STR repeat units per target DNA strand is indicated in each case (i.e. 2-16) and assigned to the groups as defined in Table 1 (i.e. A-J). For each group of target DNA strands with a particular number of STR repeat units, the results achieved with the utilized kits c3), e), d), or b3) are indicated as vertical-bar graphs (in this order). Alternatively, the four vertical-bar graphs can be named FF, FB, BF, or BB (in this order) according to the utilized flanking oligos "F" and/or blocking oligos B. Above each vertical-bar graph, the expected theoretical number of STR probe P1 oligonucleotides hybridizing per target DNA strand is indicated. On the vertical axis of the diagrams in FIG. 12, the relative fluorescence signal (the quotient of the measured intensities FAM/Cy5) is indicated as vertical bars for each one of the 60 Experiments.

FIG. 12A shows the target DNAs of the groups A (2-3 STR repeats) and B (4-6 STR repeats) as referred to in the Table 1. A perfect match for the tetramer STR probe P1 on the target DNA 5 would result, if for hybridization the number of STR repeat units in the target DNA is at least 4. It was thus expected that the target DNAs of the group A will show no hybridization of the STR probe P1 and that the target DNAs of the group B will only show hybridization of the STR probe P1 for kit c3). The height of the vertical-bar graphs (indicating the relative fluorescence signals) representing the use of kit c3) in the group B is strikingly higher than the height of the vertical-bar graphs representing the use of one of the kits e), d), or b3). Nevertheless, there is some noticeable hybridization of the STR probe P1 detectable in group A (which is considered a background signal: if compared with the results of group B, very little signal is achieved). In consequence, the results expected for the groups A and B are regarded as clearly verified.

FIG. 12B shows the target DNAs of the groups C (7 STR repeats), D (8 or 9 STR repeats), E (10 STR repeats), and F (11 STR repeats) as referred to in the Table 1. A perfect match of the 16-mer STR probe P1 on the target DNA would result, if for hybridization the number of STR repeat units in the target DNA is at least 4 (one STR probe P1 oligonucleotide hybridizing per target DNA strand) or 8 (two STR probe P1 oligonucleotides hybridizing per target DNA strand).

It was thus expected that the target DNAs of the group C will show hybridization of one STR probe P1 oligonucleotide per target DNA strand when utilizing the kits c3), e), or d) and no hybridization of the STR probe P1 when utilizing the kit b3). The height of the vertical-bar graphs (indicating the relative fluorescence signals) representing the use of the kits c3), e), or d) in the group C is strikingly higher than the height of the vertical-bar graph representing the use of the kit b3). It was also expected that the target DNAs of the group D will show hybridization of two STR probe P1 oligonucleotides per target DNA strand when utilizing the kit c3), hybridization of one STR probe P1 oligonucleotide per target DNA strand when utilizing the kits e) or d), and no hybridization of the STR probe P1 when using the kit b3). The height of the vertical-bar graph (indicating the relative fluorescence signal) representing the use of the kit c3) in the group D is about double the height of the vertical-bar graphs representing the use of the kits e) or d); the height of the vertical-bar graph (indicating the relative fluorescence signal) representing the use of the kit b3) is considerably lower than the height of the vertical-bar graphs representing the use of the kits e) or d). Even if there is some noticeable hybridization of the STR probe P1 detectable in group D when utilizing the kit b3), if compared with the results of the other kits very little signal is achieved, however. In consequence, the results expected for the groups C and D are regarded as clearly verified.

It was also expected that the target DNAs of the group E will show hybridization of two STR probe P1 oligonucleotide per target DNA strand when utilizing the kit c3) and hybridization of one STR probe P1 oligonucleotide per target DNA strand when utilizing the kits e), d), or b3). The height of the vertical-bar graphs (relative fluorescence signals) representing the use of the kits c3) in the group E is about double the height of the vertical-bar graphs representing the use of the kits e), d) or b3). In consequence, the results expected for the group E are regarded as clearly verified.

It was further expected that the target DNAs of the group F will show hybridization of two STR probe P1 oligonucleotides per target DNA strand when utilizing the kits c3), e), or d) and hybridization of one STR probe P1 oligonucleotide per target DNA strand when utilizing the kit b3). The height of the vertical-bar graphs (indicating the relative fluorescence signals) representing the use of the kits c3), e), or d) in the group F is about double the height of the vertical-bar graph representing the use of the kit b3). In consequence, the results expected for the group F are regarded as clearly verified.

FIG. 12C shows the groups G (12-13 STR repeats), H (14 STR repeats), I (15 STR repeats), and J (16 STR repeats) of target DNA as referred to in the Table 1. A perfect match for the tetramer STR probe P1 on the target DNAs would result, if for hybridization the number of STR repeat units in the target DNA is at least 4 (one STR probe P1 oligonucleotide hybridizing per target DNA strand), 8 (two STR probe P1 oligonucleotides hybridizing per target DNA strand), 12 (three STR probe P1 oligonucleotides hybridizing per target DNA strand), or 16 (four STR probe P1 oligonucleotides hybridizing per target DNA strand).

It was expected that the target DNAs of the group G will show hybridization of three STR probe P1 oligonucleotides per target DNA strand when utilizing the kit c3), hybridization of two STR probe P1 oligonucleotides per target DNA strand when utilizing the kits e) or d), and hybridization of one STR probe P1 oligonucleotide per target DNA strand when utilizing the kit b3). The height of the vertical-bar graphs (indicating the relative fluorescence signals) representing the use of the kits e) or d) in the group G in each case is about equal and double the height of the vertical-bar graphs representing the use of the kit b3). The height of the vertical-bar graph (indicating the relative fluorescence signal) representing the use of the kit c3) in the group G in each case is considerably higher than the height of the vertical-bar graphs representing the use of the kits e) or d) and about triple the height of the vertical-bar graphs representing the use of the kit b3). In consequence, the results expected for the group G are regarded as verified.

It was expected that the target DNAs of the group H will show hybridization of three STR probe P1 oligonucleotides per target DNA strand when utilizing the kit c3) and hybridization of two STR probe P1 oligonucleotides per target DNA strand when utilizing the kits e), d), or b3). The height of the vertical-bar graphs (indicating the relative fluorescence signals) representing the use of the kits e), d), or b3) in the group H is about equal. The height of the vertical-bar graph (relative fluorescence signal) representing the use of the kit c3) in the group H is considerably higher than the height of the vertical-bar graphs representing the use of the kits e), d) or b3). In consequence, the results expected for the group H are regarded as verified.

It was expected that the target DNAs of the group I will show hybridization of three STR probe P1 oligonucleotides per target DNA strand when utilizing the kit c3), e), or d) and hybridization of two STR probe P1 oligonucleotides per target DNA strand when utilizing the kit b3). The height of the vertical-bar graphs (indicating the relative fluorescence signals) representing the use of the kits c3), e), or d) in the group I is about equal. The height of the vertical-bar graph (relative fluorescence signal) representing the use of the kit b3) in the group I is considerably lower than the height of the vertical-bar graphs representing the use of the kits c3, e), or d). In consequence, the results expected for the group I are regarded as verified.

It was expected that the target DNAs of the group J will show hybridization of four STR probe P1 oligonucleotides per target DNA strand when utilizing the kit c3) (compare with FIG. 7), hybridization of three STR probe P1 oligonucleotides per target DNA strand when utilizing the kit e), or d) (compare with FIG. 9 or 10) and hybridization of two STR probe P1 oligonucleotides per target DNA strand when utilizing the kit b3) (compare with FIG. 8). The height of the vertical-bar graphs (indicating the relative fluorescence signals) representing the use of the kits e) or d) in the group J is about equal and considerably higher than the height of the vertical-bar graph representing the use of the kit b3). The height of the vertical-bar graph (relative fluorescence signal) representing the use of the kit c3) in the group J is considerably higher than the height of the vertical-bar graphs representing the use of the kits e) or d). In consequence, the results expected for the group) are regarded as verified.

The above analysis has been discussed on the base of the FIG. 12, which summarizes the relative ratios of FAM to Cy5 fluorescence obtained from each hybridization reaction. Since four ratios have been acquired for each target DNA, the target DNAs can be divided into the 10 groups A-J thus providing an indication of the genotype. The reduction in hybridization efficiency of the STR probe P1 with increased repeat numbers (see particularly FIG. 12C) might be the result that here, more ways for STR probe P1 oligonucleotides to bind to the target repeat sequence are possible. A reduction in hybridization efficiency might be predicted for a selected STR locus (e.g. by using a respective model system for that STR locus), or might be determined based on the results of the differential hybridization experiments. Such a reduction might be overcome by increasing the ratio of STR probes P1 to DNA targets. The hybridization efficiency of the 16-mer STR probe P1 is estimated to be probably less that 25%.

The various STR probes, reference probes, blockers and flankers, which are suitable for carrying out the method according to the present invention, are characterized in more detail in the following:

The STR probe P1,P1':
is an oligonucleotide, which consists of a sequence complementary to the sequence of the repeat unit of the selected STR;
the complementary sequence consists of a specific number n of repeat units,
the length of the STR probe oligonucleotide is chosen to provide a $T_m$ which is sufficient to ensure a stable hybridization to the single stranded target DNA under the selected respective experimental hybridization conditions; (if e.g. the STR is a tetramer repeat, the preferred specific number n is preferably at least 4, because n=3 (12 nucleotides in length) would result in a very low $T_m$; preferably, the STR probe oligonucleotide comprises at least 15 nucleotides;
the number of complementary repeat units in an STR probe P1 depends from the type of selected STR and the desired length of the STR probe, because not all STR's are simple repeats; preferably, the STR probe comprises the complete sequence of the repeat unit,
is labeled with a marker of a first fluorescence (e.g. FAM); this first fluorescent label might be coupled to the STR probe oligonucleotide according to the knowledge of the skilled person, e.g. at the 5'- or at the 3'-end of the oligonucleotide;
in case an STR with complex repeat units shall be analyzed, two or more STR probes P1, P1', . . . might be used which differ in their sequence or in their comprised number of complementary repeat units. Such two or more STR probes P1,P1', . . . might be used in a single hybridization experiment. Here, each different STR probe P1, P1' preferably comprises a different fluorescent label. Alternatively, such two or more STR probes P1,P1', . . . might be used in different hybridization experiments. In this case, the different STR probes P1,P1', . . . might comprise the same or a different fluorescent label.

Using two or more distinct STR probes PI,PI', . . . has the advantage e.g. to allow testing for the presence or absence of a specific motif which is known to occur in variants of a selected STR. To mention an example here: The human TH01 STR locus has naturally occurring alleles between 3 and 13 repeats of the motif 5'-AATG-3', but also has infrequently occurring variants including the so called "6.3" allele having the sequence SEQ ID NO 24: 5'-(AATG)3ATG (AATG)r3'. For detecting this TH01 specific sequence, an additional STR probe PI' might be used that is complementary to this specific motif (e.g. consisting of the sequence SEQ ID NO 25: 5'-(CATThCAT(CATTh-3') and perform a respective hybridization experiment using this probe to ascertain presence of the "6.3" allele.

The reference probe P2:
is an oligonucleotide labeled with a marker of a second fluorescence (e.g. Cy5), this second fluorescent label is different from the fluorescent label(s) of the STR probe(s) P1,P1';
serves for determining the amount of DNA present and available for hybridization, and for normalizing the measured signal of bound STR probe P1, P1' to the measured signal of bound reference probe. Normalizing in the present context means a correlation of the measured fluorescence intensity of the bound STR probe P1,P1' to the measured fluorescence intensity of the reference probe P2, to obtain a relative fluorescence signal for each distinct hybridization experiment. Based on this, the number of STR probe P1,P1' oligonucleotides bound per target DNA strand in each hybridization experiment may be determined, and a direct comparison of the signals measured in different hybridization experiments is enabled;
comprises (preferably consists of) a sequence complementary to the 5'- or 3'-flanking sequence of the target DNA, but without sequences of STR probe P1,P1', of the blockers B1,B2 or of the flankers F1,F2; could be contiguous with the flankers F1,F2; however some distance to the flanker binding site is preferred;
must not reach into the sequence of the PCR primer that is used to generate the amplicon;
does not have a minimum or maximum length; the melting point $T_m$ should be sufficient that binding is stoichiometric at experimental temperature;
is used in every hybridization experiment.

The blockers B1,B2:
at least two blockers B1,B2 are required for detecting the number of repeat units in a selected STR on a single stranded target DNA; each blocker being an oligonucleotide;
are used in addition to the STR probe P1 and the reference probe P2 in at least two of at least three differential hybridization experiments, which are preferably carried out in parallel;
each blocker B1,B2 comprises a sequence complementary to the sequence of at least one repeat unit of the selected STR, the complementary sequence consists of a specific number of repeat units. The number of repeat units preferably is depending on the number of possible repeat units for a selected STR, on the number of nucleotides per repeat unit, and on the design of the STR probe P1,P1'. Generally, there could be any number of repeat units;
each blocker comprises a sequence complementary to one of the flanking regions (5'- or 3' flanking region) of the target DNA; preferably, the at least two blockers B1,B2, which are used in the first differential hybridization experiments, are designed as a pair of blockers B1,B2, each binding to the other flanking region of the STR upon hybridization, so that repeat units of both outer regions of the selected STR may be protected by the blocker B1,B2 from being bound by the STR probe P1,P1' in at least one experiment. More preferably, a first blocker B1 comprises a sequence complementary to a sequence of the 5' flanking region of the STR and to at least one of the STR repeat units adjacent to that 5' flanking region, and a second blocker B1 correspondingly comprises a sequence complementary to a sequence of the 3' flanking region of the STR and to at least one of the STR repeat units adjacent to that 3' flanking region;
in case the results of the first three differential hybridization experiments do not allow an exact deduction of the number of repeat units in the selected STR, additional blockers B3,B4 etc. may be used to protect a different number of repeat units in the selected STR adjacent to the flanking regions; each additional blocker is used in additional, separate hybridization experiments, and is designed to replace one of the initially used blockers B1,B2.
do not comprise a fluorescent label;
when used in a control experiment together with the STR probe oligo P1, enters a competitive, stronger binding.

The flankers F1,F2:
each flanker is an oligonucleotide which consists of a sequence complementary to a 5'- or 3' flanking sequence of the selected STR on the target DNA strand;
each flanker F1,F2 is used to reduce any intramolecular secondary structure of the single stranded target DNA from which the antisense strand was stripped away and removed, thus, one or more flankers are optionally used when secondary structures in the single stranded target DNA;
each flanker F1,F1 preferably has a length (e.g. 25 nucleotides) that is designed to hybridize at the chosen hybridization temperature of the experiments (specific $T_m$ not being a critical factor);
if being a 5'-flanking oligo, comprises (preferably consists of) a sequence complementary to the 5' flanking sequence of a selected STR of the single DNA strand;
two flankers F1,F2 may used as a set of 3'- and 5'-flanking oligonucleotides, wherein the 3'-flanking oligo comprises (preferably consists of) a sequence complementary to the 3' flanking sequence of the selected STR of the single DNA strand, and the 5'-flanking oligo comprises (preferably consists of) a sequence complementary to the 5' flanking sequence of the selected STR of the single DNA strand;
do not comprise sequences that are complementary to the repeat unit sequence, do not comprise sequences of the reference probe P2, but preferably comprise a sequence (most preferably consists of a sequence) which is the same as the flanking sequence portion of one of the blocker B1,B2;
do not comprise a fluorescent label.

When carrying out the method of the present invention, the number of repeat unit sequences of the target DNA available for the STR probe P1,P1' for binding is reduced by the addition of one or more blockers B1,B2. When the number of repeat units in the blocking oligo is known, the number of repeat units which are not available any more after binding of the blocking oligo is known, too. In a particularly preferred embodiment, for the 3'-end and for the 5'-end of the STR fragment of the target DNA, one blocking oligo B1,B2 or one flanking oligo F1,F2 may be used, to ensure that the target DNA remains in the single stranded, open formation. Thus, the reduction of available repeat units on the target DNA preferably results in a reduction of fluorescence intensity compared to an experiment carried out only with the STR probe P1,P1' and the reference probe P2 alone but without blocker B1,B2, and the measured difference of fluorescence intensity of bound STR probe P1,P1' is used to deduce the number of repeats in the STR (comparison of max. intensity$_{STR\ probe\ alone}$ vs. reduced intensity$_{STR\ probe+blocker}$).

Insert probes P3:
An insert probe P3 (see FIG. 11) is a specific oligonucleotide probe for "islands" of non-repeat nucleotide sequence within the structure of the STR repeat region (in the following it is referred to these as "more complex" STR's) of a single strand target DNA.

The Insert Probe P3:
- comprises a specific sequence that is designed to bind specifically at the "island" within the STR repeat region at the selected assay temperature; depending on the nature and sequence of the "island" in the selected STR, one or more insert probes P3, P3' may be used;
- contains the base(s) complementary to the island;
- is preferably labeled with a third fluorescent label (e.g. Cy3) when used together with at least one STR probe P1,P1' and the reference probe P2 in one single hybridization experiment; alternatively, in case the insert probe P3 is not used together with an STR probe P1,P1' in one single experiment, the insert probe P3 may be labeled with the first fluorescent label or with a third fluorescent label,
- can have two flanking complements to STR repeats (e.g. two repeat units on both ends of the insert probe P3) or possibly even only a portion of a complement to an STR repeat (on one or both ends of the insert probe P3;
- is used for those loci where an "island" might be found;
- has a known insert sequence; the specific sequences of possible alleles have been published and John Butler at NIST maintains a database of such core loci at (nist.gov) (one allele being CSF1PO). The FBI has published thirteen core loci for the Combined DNA Index System (CODIS) database. STR Fact Sheets for all thirteen loci are available on-line (For more information, see: Butler, J. M. (2006) Genetics and genomics of core STR loci used in human identity testing. J. Forensic Sci. 51(2): 253-265).

In general, the oligos (blockers and probes) are designed so that each possible STR can be uniquely identified with a minimum number of probes. For carrying out the above discussed experiments, a number of oligonucleotides have been chosen for model the CSF1PO test system (5'-AGAT-375'-ATCT-3' repeat flanked by artificial sequences). These oligonucleotides are described by the sequence listing attached to this patent application. This sequence listing comprises:

SEQ ID: NO 1, a reference target strand with 5 AGAT repeats (not synthesized);
SEQ ID: NO 2, a 16-mer probe to ATCT repeat (STR probe P1);
SEQ ID: NO 3, a 20-mer probe to ATCT repeat;
SEQ ID: NO 4, a 25-mer 5'-complementary oligo (flanking oligo F1);
SEQ ID: NO 5, a 25-mer 5'-blocking oligo (blocking oligo B1);
SEQ ID: NO 6, a 25-mer 3'-complementary oligo (flanking oligo F2);
SEQ ID: NO 7, a 25-mer 3'-blocking oligo (blocking oligo B2);
SEQ ID: NO 8, a 25-mer 3'-reference oligo (reference probe P2);
SEQ ID: NO 9, a target DNA with 2 5'-ATCT-3' repeats;
SEQ ID: NO 10, a target DNA with 3 5'-ATCT-3' repeats;
SEQ ID: NO 11, a target DNA with 4 5'-ATCT-3' repeats;
SEQ ID: NO 12, a target DNA with 5 5'-ATCT-3' repeats;
SEQ ID: NO 13, a target DNA with 6 5'-ATCT-3' repeats;
SEQ ID: NO 14, a target DNA with 7 5'-ATCT-3' repeats;
SEQ ID : NO 15, a target DNA with 8 5'-ATCT-3' repeats;
SEQ ID : NO 16, a target DNA with 9 5'-ATCT-3' repeats;
SEQ ID : NO 17, a target DNA with 10 5'-ATCT-3' repeats;
SEQ ID : NO 18, a target DNA with 11 5'-ATCT-3' repeats;
SEQ ID : NO 19, a target DNA with 12 5'-ATCT-3' repeats;
SEQ ID : NO 20, a target DNA with 13 5'-ATCT-3' repeats;
SEQ ID : NO 21, a target DNA with 14 5'-ATCT-3' repeats;
SEQ ID : NO 22, a target DNA with 15 5'-ATCT-3' repeats;
SEQ ID : NO 23, a target DNA with 16 5'-ATCT-3' repeats
SEQ ID : NO 24, a target DNA variant with 6 AATG repeats and an ATG motif according to the human TH01 STR 6.3 allele; and
SEQ ID : NO 25, A 19-mer probe to TH01 STR 6.3 allele variant.

The mixtures or kits used to analyze any STR loci are very dependant on the sequence of the STR loci. But, to analyze one unknown STR locus, one would need to perform at least 3 differential hybridization experiments as follows:

Exp 1: one STR probe* P1,P1'; one reference probe* P2;
Exp. 2; one STR probe* P1,P1'; one reference probe* P2, one blocker B2,B1;
Exp. 3: one STR probe* P1,P1'; one reference probe* P2, both blockers B1,B2.

The asterix (*) refers to probes that contain a fluorescent label. Each label within a single experiment must be different. If an STR locus contains an insert ("island"), then all three experiments would also contain an insert probe P3, also labeled. More complex STRs might also require a third STR probe P1" of a different length (also fluorescently labeled) used in an additional differential hybridization experiment and/or additional differential hybridization experiment(s) using different length blocker(s).

By directly comparing the relative signals obtained in the different hybridization experiments—thus, by directly comparing the number of STR probe P1,P1' oligonucleotides bound per target DNA strand in the at least three differential hybridization experiments, in which the number of available repeat units is systematically reduced by the differential use of STR probe P1,P1' and blocker B1,B2—the number of repeat units in the selected STR may be deduced.

In case the exact number of repeat units in a selected STR might not be deduced using the at least three hybridization experiments, further supplementary differential hybridization experiments are required. Such further hybridization experiments would include the alternative use of one, two or more additional blockers B3,B4, which comprise a sequence complementary to a different number of repeat units compared to the blockers B1,B2, for systematically changing the repeat units on the target DNA available for the binding of STR probe oligonucleotides. Alternatively, such further hybridization experiments would include the use of an additional STR probe P1', P1", which differs in the comprised number of complementary repeat units (as discussed above). In a further alternative, such further hybridization experiments would include the use of one or more insert probes P3 to detect e.g. one or more STR specific non-repeat sequences. Depending on the selected STR to be analyzed, all or an appropriate combination of such supplementary hybridization experiments might be used to analyze how many STR probes P1,P1' are able to bind to the target STR sequence in the different situations created by the differential use of STR probe P1,P1', blockers B1,B2,B3,B4, and/or insert probe P3, thereby deducing—if necessary in the stepwise hybridization approach—the exact number of repeat units in the selected STR.

For example, to interrogate an STR comprising simple repeat units in an unknown number, supplementary follow up hybridization experiment might be designed to include the use of additional blockers B3, B4, etc. which are configured with respect to their sequence so that in each experiment, a different number of STR repeat units is available for the STR probe P1,P1'. Preferably, the number of available repeat units is systematically reduced in these supplementary hybridization experiments by correspondingly increasing the number of repeat units complementary to the selected STR target DNA in the used blocking oligonucleotides. Preferably, pairs of blockers B1,B2/B3, B4/etc. are used to systematically reduce the available repeat units in the initial experiments and in the supplementary experiments. In a particularly preferred embodiment, the pairs of blockers B1,B2/B3,B4/, . . . used are designed to cover the full range of expected naturally occurring repeat numbers. This set of experiments (including the initial three hybridization experiments and the optional supplementary experiments) would then enable to deduce the number of repeat units in the selected STR by comparing the number of bound STR probe P1,P1' oligonucleotides per DNA molecule with the provided blocker configuration.

Alternatively, or additionally, such an experimental set of hybridization experiments could be repeated using another STR probe P1' of different length, analyzed again in the same way, and the results are then compared with each other, e.g. to confirm the previously made deduction of the number of repeat units present in the selected STR.

In case an STR is selected for the analysis from which it is known that naturally, one or more rare alleles might occur (as e.g. the 5'-ATG-3' island in the TH01 X.3 alleles discussed above), then other supplementary experiment(s) might be carried out using one or more insert probes P3 specific for this island. In this way, the presence of such "islands" may be detected with one or more supplementary hybridization experiments. Furthermore, the number of such islands may be counted when comparing the fluorescent signal obtained from the insert probe P3 to the fluorescent signal obtained from the reference probe P2.

For distinguishing alleles of one particular STR, an example is given in FIG. 13. When inspecting FIG. 13, one should keep in mind, that all results are displayed as a ratio of the repeat signal (fluorescence intensity of bound STR probes P1) to the total DNA signal (fluorescence intensity of bound reference probes P2). For heterozygous samples however, the outputs would represent averages of the signals from each of the two alleles. This provides the opportunity for signals to be at half steps from the homozygous samples (i.e. 0.5, 1.5, 2.5, etc)

FIG. 13 represents the predicted probe signal ratios obtained from a set of experiments when the sample is not necessarily homozygous for STR repeat number. The table is explained as follows. We assume here that the sample examined will be biallelic as it is in human DNA, i.e. each of two copies of the examined STR locus have an independent number of STR repeats and are homozygous if the repeat numbers are equal or heterozygous if the repeat numbers are different. Across the top of the table are the number of repeats on allele 1 (5 through 16 in this example) and down the left side of the table are the number of repeats on allele 2 (also 5 through 16). Predicted probe signal ratios are displayed for a set of 6 measurements for each combination of alleles: either no blocker, 1 blocker, or 2 blockers are used in combination with either a 20-mer or 16-mer STR probe P1,P1'. The blockers in these experiments each can hybridize with and "block" with the 3 terminal repeats from either end of the repeat region (12 nucleotides worth). Thus for each combination of allele 1 and allele 2, 6 signal measurements are made, and the predicted ratio of these six signal measurements is shown on a horizontal in the table. For example, for the combination of 11 STR repeat units (allele 1) and 15 STR repeat units (allele 2), we would expect the signal ratios to be 2.5:2.5:1.5:2.5:1.0:1.5 for experiments with a 20-mer STR probe and no blocker, 16-mer STR probe and no blocker, 20-mer STR probe and one blocker, 16-mer STR probe and one blocker, 20-mer STR probe and two blockers, and 16-mer STR probe and two blockers, respectively. The underscored values on the diagonal in the table represent the homozygous condition where allele 1 and allele 2 have the same number of STR repeat units. A unique pattern is still provided by each possible allelic combination.

What is claimed is:

1. A method of deducing the number of repeat units in a selected short tandem repeat (STR) in a genomic sample, the method comprising the steps of:
   a) providing at least:
      a1) a single stranded target DNA generated from a genomic sample comprising a selected STR;
      a2) an STR probe (P1) with a first fluorescent label, the STR probe (P1) being an oligonucleotide which comprises a sequence complementary to a defined number of repeat units of the selected STR on the single stranded target DNA;
      a3) a reference probe (P2) with a second fluorescent label, which is different from the first fluorescent label, the reference probe (P2) being an oligonucleotide which comprises a sequence complementary to a 5'- or a 3'-flanking sequence of the selected STR on the single stranded target DNA; and
      a4) two blockers (B1 and B2) which are oligonucleotides, wherein a first blocker (B1) comprises a sequence complementary to a sequence of the 5' flanking region of the STR and to at least one of the STR repeat units adjacent to that 5' flanking region, and wherein a second blocker (B2) comprises a sequence complementary to a sequence of the 3' flanking region of the STR and to at least one of the STR repeat units adjacent to that 3' flanking region;
   b) carrying out at least the following three differential hybridization experiments by mixing in each experiment an amount of the single stranded target DNA with:

b1) the STR probe (P1) and the reference probe (P2), and allowing hybridization to the single stranded target DNA in a first differential hybridization experiment;
b2) the STR probe (P1), the reference probe (P2) and one of the two blockers (B1 and B2), and allowing hybridization to the single stranded target DNA in a second differential hybridization experiment; and
b3) the STR probe (P1), the reference probe (P2) and the two blockers (B1 and B2), and allowing hybridization to the single stranded target DNA in a third differential hybridization experiment;
c) measuring for each differential hybridization experiment the intensity of the fluorescence provided by the STR probe (P1) bound to the repeat units of the selected STR;
d) measuring for each differential hybridization experiment the intensity of the fluorescence provided by the reference probe (P2) bound to one of the flanking sequences of the single stranded target DNA;
e) correlating for each differential hybridization experiment the fluorescence intensity of the STR probe (P1) measured in step c) to the fluorescence intensity of the reference probe (P2) measured in step d), thereby determining for each differential hybridization experiment the number of STR probe oligonucleotides (P1) bound per target DNA strand, and
f) comparing the numbers of STR probe oligonucleotides (P1) bound per target DNA strand determined in the differential hybridization experiments to deduce the number of repeat units in the selected STR on the single stranded target DNA strand.

2. The method of claim 1,
wherein in step a4), a third blocker (B3) is provided, wherein this third blocker (B3) is an oligonucleotide which comprises a sequence complementary to a sequence of the 5' flanking region of the STR and to a number of the STR repeat units adjacent to that 5' flanking region which is different from the number of repeat units in the first blocker (B1), and wherein the method comprises a step b4), in which an amount of the single stranded target DNA is mixed with the STR probe (P1), the reference probe (P2) and the third blocker (B3), and the STR probe (P1), the reference probe (P2) and the third blocker (B3) are allowed to hybridize to the single stranded target DNA in a differential hybridization experiment.

3. The method of claim 1,
wherein in step a4), a further blocker (B4) is provided, wherein this further blocker (B4) is an oligonucleotide which comprises a sequence complementary to a sequence of the 3' flanking region of the STR and to a number of the STR repeat units adjacent to that 3' flanking region which is different from the number of repeat units in the second blocker (B2),
and wherein the method comprises a step (b4), in which an amount of the single stranded target DNA is mixed with the STR probe (P1), the reference probe (P2) and the further blocker (B4), and the STR probe (P1), the reference probe (P2) and the further blocker (B4) are allowed to hybridize to the single stranded target DNA in a differential hybridization experiment.

4. The method of claim 1,
wherein in step a4), at least a third and fourth blocker (B3 and B4) are provided which are oligonucleotides, wherein the third blocker (B3) comprises a sequence complementary to a sequence of the 5' flanking region of the STR and to a number of the STR repeat units adjacent to that 5' flanking region which is different from the number of repeat units in the first blocker (B1), and wherein the fourth blocker (B4) comprises a sequence complementary to a sequence of the 3' flanking region of the STR and to a number of STR repeat units adjacent to that 3' flanking region which is different from the number of repeat units in the second blocker (B2),
and wherein the method comprises the steps of:
b4) mixing an amount of the single stranded target DNA with the STR probe (P1), the reference probe (P2) and the third blocker (B3), and allowing hybridization to the single stranded target DNA in a fourth differential hybridization experiment;
b5) mixing an amount of the single stranded target DNA with the STR probe (P1), the reference probe (P2) and the fourth blocker (B4), and allowing hybridization to the single stranded target DNA in a fifth differential hybridization experiment; and
b6) mixing an amount of the single stranded target DNA with the STR probe (P1), the reference probe (P2) and the third and fourth blockers (B3 and B4), and allowing hybridization to the single stranded target DNA in a sixth differential hybridization experiment.

5. The method of claim 1, comprising the further steps of providing at least one insert probe (P3) with a third fluorescent label, the at least one insert probe (P3) being an oligonucleotide comprising a sequence complementary to a non-repeat nucleotide sequence within the repeat sequence of the selected STR on the single stranded target DNA;
and using the at least one insert probe (P3) in a separate differential hybridization experiment or in the hybridization experiment of step b1) for determining the presence or absence of the repeat nucleotide sequence within the repeat sequence of the selected STR on the single stranded target DNA.

6. The method of claim 1, wherein in step a2), two STR probes (P1 and P1') are provided, each consisting of a sequence complementary to a different, defined number of repeat units of the selected STR on the single stranded target DNA, wherein in steps b1)-b3), the first STR probe (P1) is used, and wherein further hybridization experiments are carried out in which the second STR probe (P1') is used instead of the first STR probe (P1).

7. The method of claim 1, further comprising the steps of providing a set of flankers (F1 and F2) which are oligonucleotides, wherein a first flanker (F1) comprises a sequence complementary to a sequence of the 5' flanking region of the STR, and wherein a second flanker (F2) comprises a sequence complementary to a sequence of the 3' flanking region of the STR;
and using at least one of the flankers (F1 or F2) in those differential hybridization experiments in which no or one blocker (B1 or B2) is used, to hybridize to a 5'- or 3'-flanking region of the selected STR on the single stranded target DNA which is not covered by a blocker (B1 or B2).

8. The method of claim 1, further comprising the steps of providing a set of polymerase chain reaction (PCR) oligonucleotides for carrying out PCR amplification of the genomic sample with the selected STR, amplifying the genomic sample with the selected STR sequence provided in step a1) by PCR using the set of PCR oligonucleotides, denaturing the amplified double stranded sample DNA to generate single stranded DNA, and selecting and separating a single stranded target DNA for use in the differential hybridization experiments.

9. The method of claim 1, wherein the genomic sample provided in step a1) is a human genomic sample.

10. The method of claim 1, wherein the reference probe (P2) is labeled with Cy5 at the 3'-end of the oligonucleotide.

11. The method of claim 1, wherein the STR probe (P1) is labeled with the first fluorescent label at the 3'-end of the oligonucleotide, the first fluorescent label being 6-Carboxyfluorescein, which is a fluorescent derivative and a member of xanthene fluorescent dyes.

12. The method of claim 1, wherein the STR probe (P1) consists of complementary sequences to the selected STR.

13. The method of claim 1, wherein the reference probe (P2) comprises a sequence complementary to the 5' or 3' flanking sequence of the target DNA without sequences of the selected STR.

14. The method of claim 7, wherein the reference probe (P2) comprises a sequence complementary to the 5' or 3' flanking sequence of the target DNA, without sequences of the selected STR and without sequences of the flanking oligonucleotides (F1 or F2).

\* \* \* \* \*

SEQUENCE LISTING

```
<160> NUMBER OF SEQ ID NOS: 23

<210> SEQ ID NO 1
<211> LENGTH: 105
<212> TYPE: DNA
<213> ORGANISM: Artificial Sequence
<220> FEATURE:
<223> OTHER INFORMATION: Synthetic

<400> SEQUENCE: 1
tttttttttt ctattgggag gtcattgtaa agaggagata gatagataga tagataacag        60
ggtctgacac aggaaatgct gtccaagtgt gcaccaggag atagt                       105

<210> SEQ ID NO 2
<211> LENGTH: 16
<212> TYPE: DNA
<213> ORGANISM: Artificial Sequence
<220> FEATURE:
<223> OTHER INFORMATION: Synthetic

<400> SEQUENCE: 2
agatagatag atagat                                                        16

<210> SEQ ID NO 3
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 3
agatagatag atagatagat                                                    20

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
ctattgggag gtcattgtaa agagg                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
cattgtaaag aggagataga tagat                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
aacagggtct gcacaggaa atgct                                               25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
agatagatag ataacagggt ctgac                                              25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
gtccaagtgt gcaccaggag atagt                                              25

<210> SEQ ID NO 9
<211> LENGTH: 93
<212> TYPE: DNA
<213> ORGANISM: Artificial Sequence
<220> FEATURE:
<223> OTHER INFORMATION: Synthetic

<400> SEQUENCE: 9
```

```
tttttttttt actatctcct ggtgcacact tggacagcat ttcctgtgtc agaccctgtt    60
atctatctcc tctttacaat gacctcccaa tag                                 93
```

<210> SEQ ID NO 10
<211> LENGTH: 97
<212> TYPE: DNA
<213> ORGANISM: Artificial Sequence
<220> FEATURE:
<223> OTHER INFORMATION: Synthetic

<400> SEQUENCE: 10

```
tttttttttt actatctcct ggtgcacact tggacagcat ttcctgtgtc agaccctgtt    60
atctatctat ctcctcttta caatgacctc ccaatag                             97
```

<210> SEQ ID NO 11
<211> LENGTH: 101
<212> TYPE: DNA
<213> ORGANISM: Artificial Sequence
<220> FEATURE:
<223> OTHER INFORMATION: Synthetic

<400> SEQUENCE: 11

```
tttttttttt actatctcct ggtgcacact tggacagcat ttcctgtgtc agaccctgtt    60
atctatctat ctatctcctc tttacaatga cctcccaata g                       101
```

<210> SEQ ID NO 12
<211> LENGTH: 105
<212> TYPE: DNA
<213> ORGANISM: Artificial Sequence
<220> FEATURE:
<223> OTHER INFORMATION: Synthetic

<400> SEQUENCE: 12

```
tttttttttt actatctcct ggtgcacact tggacagcat ttcctgtgtc agaccctgtt    60
atctatctat ctatctatct cctctttaca atgacctccc aatag                   105
```

<210> SEQ ID NO 13
<211> LENGTH: 109
<212> TYPE: DNA
<213> ORGANISM: Artificial Sequence
<220> FEATURE:
<223> OTHER INFORMATION: Synthetic

<400> SEQUENCE: 13

```
tttttttttt actatctcct ggtgcacact tggacagcat ttcctgtgtc agaccctgtt    60
atctatctat ctatctatct atctcctctt tacaatgacc tcccaatag               109
```

<210> SEQ ID NO 14
<211> LENGTH: 113
<212> TYPE: DNA
<213> ORGANISM: Artificial Sequence
<220> FEATURE:
<223> OTHER INFORMATION: Synthetic

<400> SEQUENCE: 14

```
tttttttttt actatctcct ggtgcacact tggacagcat ttcctgtgtc agaccctgtt    60
atctatctat ctatctatct atctatctcc tctttacaat gacctcccaa tag          113
```

<210> SEQ ID NO 15
<211> LENGTH: 117
<212> TYPE: DNA

```
<213> ORGANISM: Artificial Sequence
<220> FEATURE:
<223> OTHER INFORMATION: Synthetic

<400> SEQUENCE: 15
tttttttttt actatctcct ggtgcacact tggacagcat ttcctgtgtc agaccctgtt    60
atctatctat ctatctatct atctatctat ctcctcttta caatgacctc ccaatag     117

<210> SEQ ID NO 16
<211> LENGTH: 121
<212> TYPE: DNA
<213> ORGANISM: Artificial Sequence
<220> FEATURE:
<223> OTHER INFORMATION: Synthetic

<400> SEQUENCE: 16
tttttttttt actatctcct ggtgcacact tggacagcat ttcctgtgtc agaccctgtt    60
atctatctat ctatctatct atctatctat ctatctcctc tttacaatga cctcccaata   120
g                                                                  121

<210> SEQ ID NO 17
<211> LENGTH: 125
<212> TYPE: DNA
<213> ORGANISM: Artificial Sequence
<220> FEATURE:
<223> OTHER INFORMATION: Synthetic

<400> SEQUENCE: 17
tttttttttt actatctcct ggtgcacact tggacagcat ttcctgtgtc agaccctgtt    60
atctatctat ctatctatct atctatctat ctatctatct cctctttaca atgacctccc   120
aatag                                                              125

<210> SEQ ID NO 18
<211> LENGTH: 129
<212> TYPE: DNA
<213> ORGANISM: Artificial Sequence
<220> FEATURE:
<223> OTHER INFORMATION: Synthetic

<400> SEQUENCE: 18
tttttttttt actatctcct ggtgcacact tggacagcat ttcctgtgtc agaccctgtt    60
atctatctat ctatctatct atctatctat ctatctatct atctcctctt tacaatgacc   120
tcccaatag                                                          129

<210> SEQ ID NO 19
<211> LENGTH: 133
<212> TYPE: DNA
<213> ORGANISM: Artificial Sequence
<220> FEATURE:
<223> OTHER INFORMATION: Synthetic

<400> SEQUENCE: 19
tttttttttt actatctcct ggtgcacact tggacagcat ttcctgtgtc agaccctgtt    60
atctatctat ctatctatct atctatctat ctatctatct atctatctcc tctttacaat   120
gacctcccaa tag                                                     133

<210> SEQ ID NO 20
<211> LENGTH: 137
<212> TYPE: DNA
<213> ORGANISM: Artificial Sequence
```

```
<220> FEATURE:
<223> OTHER INFORMATION: Synthetic

<400> SEQUENCE: 20
tttttttttt actatctcct ggtgcacact tggacagcat ttcctgtgtc agaccctgtt    60
atctatctat ctatctatct atctatctat ctatctatct atctatctat ctcctcttta   120
caatgacctc ccaatag                                                   137

<210> SEQ ID NO 21
<211> LENGTH: 141
<212> TYPE: DNA
<213> ORGANISM: Artificial Sequence
<220> FEATURE:
<223> OTHER INFORMATION: Synthetic

<400> SEQUENCE: 21
tttttttttt actatctcct ggtgcacact tggacagcat ttcctgtgtc agaccctgtt    60
atctatctat ctatctatct atctatctat ctatctatct atctatctat ctatctcctc   120
tttacaatga cctcccaata g                                              141

<210> SEQ ID NO 22
<211> LENGTH: 145
<212> TYPE: DNA
<213> ORGANISM: Artificial Sequence
<220> FEATURE:
<223> OTHER INFORMATION: Synthetic

<400> SEQUENCE: 22
tttttttttt actatctcct ggtgcacact tggacagcat ttcctgtgtc agaccctgtt    60
atctatctat ctatctatct atctatctat ctatctatct atctatctat ctatctatct   120
cctctttaca atgacctccc aatag                                          145

<210> SEQ ID NO 23
<211> LENGTH: 149
<212> TYPE: DNA
<213> ORGANISM: Artificial Sequence
<220> FEATURE:
<223> OTHER INFORMATION: Synthetic

<400> SEQUENCE: 23
tttttttttt actatctcct ggtgcacact tggacagcat ttcctgtgtc agaccctgtt    60
atctatctat ctatctatct atctatctat ctatctatct atctatctat ctatctatct   120
atctcctctt tacaatgacc tcccaatag                                      149
```